(12) United States Patent
Ahotupa

(10) Patent No.: US 8,039,263 B2
(45) Date of Patent: Oct. 18, 2011

(54) ESTIMATION AND BIOLOGICAL CONSEQUENCES OF OXIDATIVE METABOLISM

(76) Inventor: Markku Ahotupa, Turku (FI)

( * ) Notice: Subject to any disclaimer, the term of this patent is extended or adjusted under 35 U.S.C. 154(b) by 41 days.

(21) Appl. No.: 12/595,379

(22) PCT Filed: Apr. 9, 2008

(86) PCT No.: PCT/FI2008/050174
§ 371 (c)(1),
(2), (4) Date: Oct. 9, 2009

(87) PCT Pub. No.: WO2008/125724
PCT Pub. Date: Oct. 23, 2008

(65) Prior Publication Data
US 2010/0055796 A1 Mar. 4, 2010

(30) Foreign Application Priority Data
Apr. 11, 2007 (FI) .................................. 20075245

(51) Int. Cl.
*G01N 33/92* (2006.01)
*G01N 33/48* (2006.01)
(52) U.S. Cl. ............. 436/71; 436/63; 436/174; 436/178
(58) Field of Classification Search .................... 436/63, 436/71, 174, 178
See application file for complete search history.

(56) References Cited

U.S. PATENT DOCUMENTS

| 5,874,313 A | * | 2/1999 | Ahotupa ......................... 436/71 |
| 6,869,568 B2 | * | 3/2005 | Fogelman et al. ............ 422/421 |
| 2004/0241744 A1 | * | 12/2004 | Kohno et al. ................. 435/7.1 |

FOREIGN PATENT DOCUMENTS

| JP | 09033525 | * | 2/1997 |
| JP | 2004-69672 A | | 3/2004 |
| WO | WO-2005/055810 A2 | | 6/2005 |
| WO | WO-2006/014628 A1 | | 2/2006 |

OTHER PUBLICATIONS

Hurtado et al. Atherosclerosis, vol. 125, 1996, pp. 39-46.*
Ahotupa et al. Clinical Biochemistry, vol. 31, No. 4, 1998, pp. 257-261.*
Nakano et al., "Immunochemical detection of circulating oxidized high-density liprotein with antioxidized apolipoprotein A-I monoclonal antibody" Journal of Laboratory and Clinical Medicine, Jun. 2003, vol. 141, No. 6, pp. 378-384.
Nakano et al., Immunoreactive circulating oxidized HDL concentrations do not increase in patients undergoing carotid endarterectomy: A comparative study for oxidized HDL and oxidized LDL concentrations in plasma, Clinica Chimica Acta, 2007, vol. 381, pp. 179-181.
Bergt et al., "Oxidized plasma high-density lipoprotein is decreased in Alzheimer's disease", Free Radical Biology & Medicine, vol. 41, (2006), pp. 1542-1547.
Nakano et al., "NAD(P)H oxidase p22$^{phox}$ Gene C $^{242}$ T polymorphism and lipoprotein oxidation", Clinica Chimica Acta, vol. 335, pp. 101-107, 2003.
"Lipid peroxides", Published at the Centre for Cancer Education, University of Newcastle upon Tyne, Dec. 12, 1998, Retrieved from the Internet: <URL:http://cancerweb.ncl.uk/cgi-omd?lipid+peroxides abstract.
Parhami et al., "High-density lipoprotein regulates calcification of vascular cells" Circulation Research, 2002, vol. 91, pp. 570-576.
Ng., "Treating low HDL- from bench to bedside", Clinical Biochemistry, 2004, vol. 37, pp. 649-659.
Ashen et al., "Low HDL Cholesterol Levels", ACC Current Journal Review, Dec. 2005, pp. 15-16.
Mackness et al., "HDL, its enzymes and its potential to influence lipid peroxidation", Atherosclerosis, vol. 115, 1995, pp. 243-253.
Panzenbock et al., "Formation of methionine sulfoxide-containing specific forms of oxidized high-density lipoproteins", Biochimica of Biophysica Acta, vol. 1703, pp. 171-181, 2005.
Schnell et al., "Effects of a high polyunsaturated fat diet and vitamin E supplementation on high-density liporotein oxidation in humans", Atherosclerosis, vol. 159, (2001), pp. 459-466.
Kajanachumpol et al., "Levels of Plasma Lipid Peroxide Products and Antioxidant Status in Rheumatoid Arthritis", Southeast Asian J Trop Med Public Health, vol. 31, No. 2, Jun. 2000, pp. 335-338.
Santra et al., "Lipid peroxidation and vitamin E status in gestational diabetes mellitus", Journal Obstet. Gynaecol. Res., vol. 29, No. 5, Oct. 2003, pp. 300-304.

* cited by examiner

*Primary Examiner* — Maureen Wallenhorst
(74) *Attorney, Agent, or Firm* — Birch, Stewart, Kolasch & Birch, LLP.

(57) ABSTRACT

The present invention relates to monitoring of oxidative metabolism and is, particularly, directed to a method for estimation of the lipid peroxide load or the consequent inflammatory state of a subject by measuring the concentration of the subject's oxidized HDL (high density lipoprotein) lipids. In addition, the invention is also directed to methods for the elimination of lipid peroxidation products, and attenuation of the resulting oxidative stress and inflammatory state in the human body by increasing the lipid peroxide transporting capacity of HDL.

5 Claims, 7 Drawing Sheets

ESTIMATION AND BIOLOGICAL CONSEQUENCES OF OXIDATIVE METABOLISM

FIELD OF THE INVENTION

The present invention relates to monitoring of oxidative metabolism and is, particularly, directed to a method for the estimation of lipid peroxide load or the consequent inflammatory state of a subject by measuring the concentration of oxidized high density lipoprotein (HDL) lipids of the subject. In addition, the invention is also directed to methods for elimination of lipid peroxidation products, and attenuation of the resulting oxidative stress and inflammatory state in human body, by increasing the lipid peroxide transporting capacity of HDL.

BACKGROUND OF THE INVENTION

The physiological function of lipoprotein particles is to transport lipids and lipid soluble material in the bloodstream to and from the liver. Low density lipoprotein (LDL) is the main transporter of cholesterol to the peripheral tissues, while excess tissue cholesterol is returned to the liver by reverse cholesterol transport mediated by HDL. In parallel with the transport functions, high LDL cholesterol is associated with elevated risk of cardiovascular disease, while high HDL cholesterol appears to be protective.

Along with the native lipids, LDL and HDL particles are known to contain products of lipid peroxidation. Oxidized LDL lipids may be derived from endogenous lipid peroxidation reactions, or directly from peroxidized dietary lipids. Oxidized HDL lipids, in turn, may be received directly from LDL, or from endogenous lipid peroxidation. Products of lipid peroxidation are toxic, and in many ways involved in the development of atherosclerosis. They are directly linked with macrophage accumulation, regulation of macrophage activity and foam cell formation in vessel wall, and with activation of atherosclerosis-related gene groups[1].

Peroxidized lipids are also the cause of intracellular oxidative stress and inflammatory response: Oxidative stress results in activation of nuclear factor κB (NFκB), leading to production of cytokines and other mediators of the inflammatory response. These will then elicit in the liver the synthesis of acute phase proteins, which are the common indicators of inflammatory response (FIG. 1). Interestingly, experimental studies seem to indicate that cholesteryl ester hydroperoxides in HDL can be taken up by the liver[2]. In addition to the central role in lipid metabolism, recent studies have shown that HDL can have anti-inflammatory effects by counteracting the proinflammatory effect of oxidized LDL[3]. The anti-inflammatory effect of HDL has been attributed to attenuation of the NFκB activation by oxidants[3].

Oxidation of HDL can be assayed either in lipid or apolipoprotein moieties of HDL. Various publications disclose measurement of the levels of oxidised apolipoprotein A-I moiety of HDL[4-6], and discuss the meaning of said levels in certain diseases. However, determination of the oxidation of the lipid moiety of HDL has not been disclosed or discussed earlier.

SUMMARY OF THE INVENTION

In the present study we describe another physiological function for HDL, and offer an alternative mechanism for the anti-inflammatory effect of HDL. In studies with human volunteers we show that HDL responds to increased concentrations of lipid peroxidation products by actively transporting excess of peroxidized lipids from tissues, and thereby exerts the antioxidant and anti-inflammatory action.

Consequently, a primary object of this invention is a method for estimating lipid peroxide load and the consequent inflammatory state in a subject, comprising measuring the concentration of oxidized high density lipoprotein (HDL) lipids in a biological sample obtained from the subject. The biological sample is appropriately a blood sample, preferably a serum or plasma sample. In specific, the method may be used for diagnosis or follow-up of treatment or study of a lipid peroxide-related condition, or of an inflammation-related condition. Such a lipid peroxide-related condition may be, for instance, ageing, neurodegeneration, atherosclerosis, cancer, diabetes or cataract. An inflammation-related condition is, for example, rheumatoid arthritis, an inflammatory bowel disease, including Crohn's disease, an inflammatory skin disease, HIV/AIDS, atherosclerosis or an autoimmune disorder.

A further object of the present invention is a method for strengthening the lipid peroxide transporting capacity of HDL, comprising increasing the concentration of HDL or enhancing the lipid peroxide sequestering capacity of the HDL particles.

DETAILED DESCRIPTION OF THE INVENTION

Figure 1:
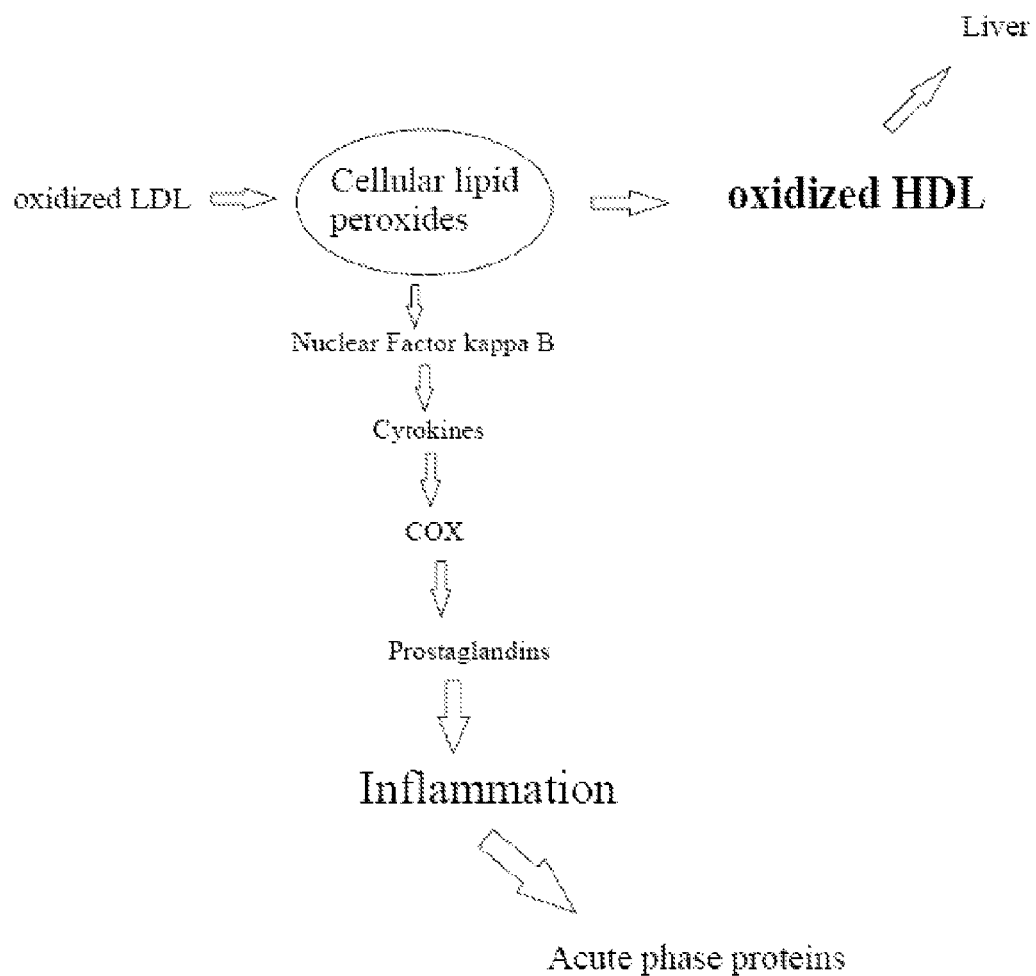
FIG. 1. Cellular lipid peroxides activate Nuclear Factor kappa B (NFκB), which leads to production of cytokines and other mediators of the inflammatory response. HDL responds to increase of peroxidized lipids, and has antioxidant and anti-inflammatory effects through active transport of excess of peroxidized lipids from tissues.

Each HDL particle contains phospholipids, cholesteryl esters, triglycerides and free cholesterol, as well as peripheral (apolipoproteins C) and integral (apolipoprotein A) protein moieties. The lipid and apolipoprotein C moieties of HDL are in continuous dynamic change between other lipoprotein particles, peripheral tissues and the liver, while the integral apolipoprotein A remains the same throughout the lifespan of the HDL particle. Measurement of "HDL oxidation" can be based on determination of oxidized HDL lipids or, alternatively, oxidatively modified apolipoprotein A. When the measurement is based on oxidized HDL lipids, it is indicative of the overall lipid peroxide load in the body (indicated by the total amount of lipid peroxides carried by HDL) and, at the same time, of the lipid peroxide transporting capacity of HDL (indicated by the amount of lipid peroxides per HDL particle). On the contrary, quantification of oxidative modifications of apolipoprotein A is indicative of protein-modifying free radical activity in vessel wall. Thus, even though the term "oxidized HDL" can be applied to both ways of determining HDL oxidation, the biological mechanisms of which they are indicative, are not the same.

Based on the data presented in this application, measurement of oxidized HDL lipids can be used for the estimation of lipid peroxide load, the resulting oxidative stress and inflammatory state. The measurement of oxidized HDL lipids can thus be applied for diagnosis, follow-up of treatment and study of lipid peroxide-related physiological and pathophysiological conditions, such as ageing, neurodegeneration, atherosclerosis, cancer, diabetes and cataract. In addition, the measurement of oxidized HDL lipids can thus be applied for diagnosis, follow-up of treatment and study of inflammation-related physiological and pathophysiological conditions, such as rheumatoid arthritis, inflammatory bowel disease (including Crohn's disease), inflammatory skin diseases, HIV/AIDS, atherosclerosis and autoimmune disorders.

Furthermore, based on the data presented in this application, strengthening of the lipid peroxide transporting capacity of HDL can thus be used for the prevention and treatment of lipid peroxide-related pathophysiological conditions, such as neurodegeneration, atherosclerosis, cancer, diabetes and cataract, and also for the prevention and treatment of inflammation-related pathophysiological conditions, such as rheumatoid arthritis, inflammatory bowel disease (including Crohn's disease), inflammatory skin diseases, HIV/AIDS, atherosclerosis and autoimmune disorders.

For the analysis of oxidized HDL lipids, HDL may first have to be isolated from serum or plasma samples. This is typically carried out, e.g., with the use of precipitation methods (such as use of the phosphotungstic acid), centrifugation methods, methods based on lipoprotein density or electrophoretic mobility of HDL. Oxidized HDL lipids can be assayed by the diene conjugation method, as thiobarbituric acid reactants, as malondialdehyde, isoprostanes, oxidized cholesterol or oxidized phospholipids. For analysis of oxidative lipid modifications of HDL, immunological methods may also be used, which are based on the use of specific antibodies recognizing various lipid oxidation-specific epitopes.

The lipid peroxide transporting capacity of HDL can be strengthened by increasing the concentration of HDL, by increasing the amount or activity of the cholesterol transfer protein, or by enhancing the lipid peroxide sequestering capacity of the HDL particles. The concentration of HDL can be increased by life style-dependent factors, drugs, or by dietary means. HDL-increasing life style-dependent factors include physical exercise, weight loss and smoking cessation. HDL increasing drugs are typically those that have been designed to treat lipid disorders, including niacin, cholesterylamine, gemfibrozil, statins and sobetirome. Dietary means for increasing HDL concentration include cutting ingestion of trans fats, increasing the proportion of polyunsaturated fatty acids and fiber in the diet, increasing the consumption of fruits, vegetables and legumes. The dietary means for increasing HDL concentration also include functional foods, where the effects are due to specific HDL-affecting ingredients. The lipid peroxide sequestering capacity of HDL particles may be enhanced by modifying the amounts or relative proportions of native lipids in various HDL lipid classes. The amounts and relative proportions of the native lipids in various HDL lipid classes can be modified by drugs affecting lipid metabolism, or by dietary means. The dietary means include supplements, or functional foods, with lipids or lipid precursors as the active ingredients.

EXPERIMENTAL

Methods

Subjects

Subjects in the first study were male, top national level endurance runners (n=24), who performed a maximal treadmill test.

Subjects in the second study were healthy volunteers of both sexes (n=13), who consumed a standard meal rich in lipid peroxides.

Subjects in the third study were healthy volunteers of both sexes (n=62), who participated in a cross-sectional study on atherosclerosis risk factors.

Subjects in the fourth study were normolipidemic healthy volunteers (n=2), reportedly having no detectable inflammatory disorders during the past 2 months.

Treadmill Test

The subjects performed a maximal run, which consisted of a velocity-incremented continuous treadmill run. The duration of each stage of the test was 2 min, whereafter the velocity was increased by 1 km/h for each consecutive stage until exhaustion. Blood samples were taken before, immediately after, as well as 15 and 90 minutes after the exercise.

Test Diets

Before the study the subjects were asked to maintain their normal lifestyle habits and not to make any changes to the diet or in the physical activity. The test subjects had a standardized breakfast in the morning at 8 o'clock. The subjects were not allowed to eat anything until 11 o'clock when the baseline (Oh) blood sample was drawn. After the baseline blood sample, subjects consumed a standard hamburger meal and 4 dl of fruit juice. Further blood samples were taken at 30, 60, 120, 240 and 360 min time points after baseline measurement. The subjects were not allowed to eat, but they were allowed to drink water during the 6 h test period.

Anti-inflammatory Treatment

The subjects were given ibuprofen (BURANA®, Orion, Espoo, Finland) as the anti-nflammatory treatment for 3 consecutive days at a dose of 3×400 mg. Blood samples were taken at 9 o'clock in the morning on days 0 (baseline value), 1, 2 and 3.

Analytical Procedures

Oxidized HDL lipids were measured by the spectrophotometric diene conjugation method in lipids extracted from isolated HDL. Isolation of HDL from serum samples was based on phosphotungstic acid precipitation. After isolation of HDL, lipids were extracted and the spectrophotometric analysis performed as described for oxidized LDL lipids[7]. The coefficients of variation (CV) for the assay (within- and between-assay precisions) were <5%.

HPLC analysis was performed with a Shimadzu 10ADVP. Luna 5µ silica column, 250×4.6 mm, was used. Detection of oxidized HDL lipids was based on UV detector operating at 234 nm. The eluent was 4% propanol in hexane, and the flow rate was 1 ml/min. Lipid classes were located by the HPLC elution volume correlations with standard samples.

Oxidized LDL lipids were measured by determining the level of baseline LDL diene conjugation. In brief, serum LDL cholesterol was isolated by precipitation with buffered heparin. Lipids were extracted from the samples and the amount of peroxidized lipids in samples was determined by degree of conjugated diene double bonds analyzed spectrophotometrically at 234 nm[3]. The coefficients of variation (CV) for the assay (within- and between-assay precisions) were <4.5%.

Cholesterol (HDL and LDL) was measured using standard enzymatic methods (Roche Diagnostics GmbH, Mannheim, Germany). HDL cholesterol concentration was measured after phosphotungstic acid precipitation.

In the first study (physical exercise) serum malondialdehyde was determined as total (free and protein-bound) malondialdehyde converted to the 2,4-dinitrophenyl-hydrazine derivative. The assay was performed with HPLC with 1,1,3,3-tetraethoxypropane as the standard. In the fourth study (anti-inflammatory treatment) malondialdehyde concentration was determined spectrophotometrically as thiobarbituric acid reactants. As a measure of lipid peroxides, malondialdehyde differs from (HDL and LDL) diene conjugation in that the former merely represents hydrophilic end products of lipid peroxidation, while the latter are hydrophobic primary products of peroxidation of polyunsaturated fatty acids.

Total peroxyl radical trapping antioxidant potential (TRAP) was estimated ex vivo by the potency of serum samples to resist ABAP-induced peroxidation. Trolox served as a standard radical scavenger. Antioxidant vitamin (α-tocopherol, γ-tocopherol, β-carotene, retinol, ubiquinol-10) concentrations were analyzed by standard HPLC procedures with UV-detection.

Results and Discussion

Figure 2:
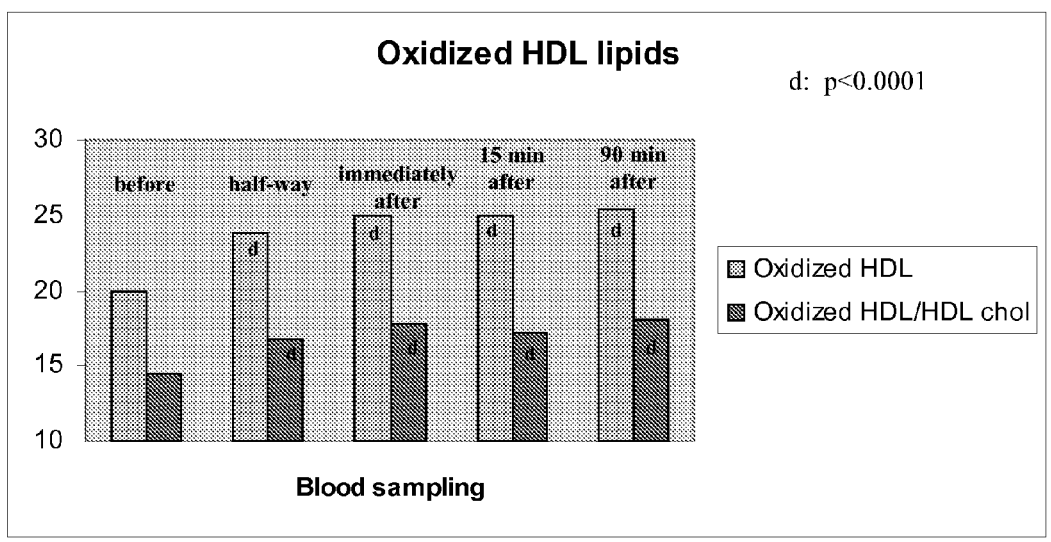
FIG. 2. Concentration of oxidized HDL lipids and the ratio of oxidized HDL lipids/HDL cholesterol are increased due to physical exercise-induced oxidative stress. The subjects, male endurance runners (n=24), performed a maximal treadmill test, and blood samples were taken before, during and after the run. Oxidized HDL lipids were measured by the diene conjugation method in lipids extracted form isolated HDL. Oxidized HDL lipids, μmol/L; oxidized HDL lipids/HDL cholesterol, μmol/mmol.
Figure 3:
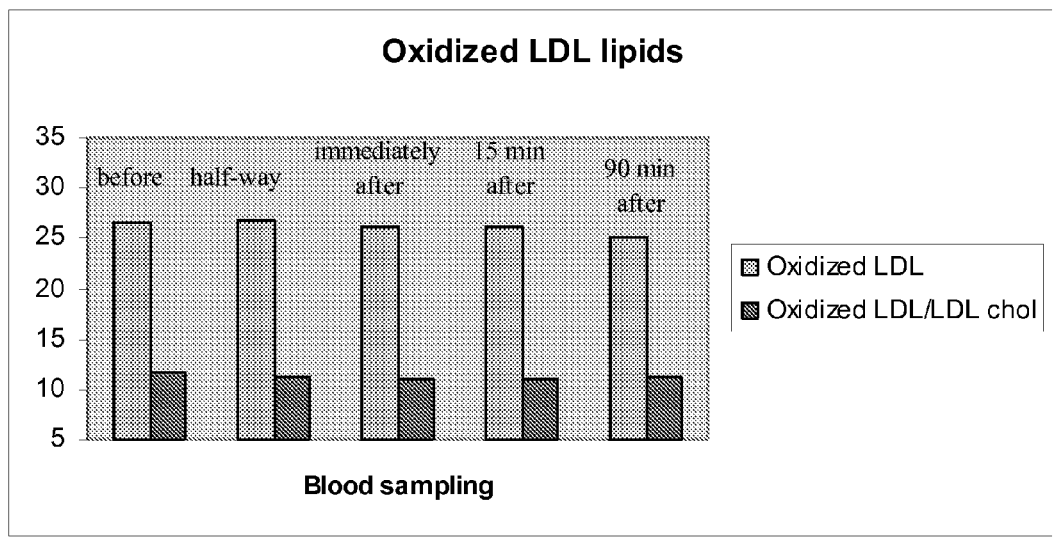
FIG. 3. Concentration of oxidized LDL lipids and the ratio of oxidized LDL lipids/LDL cholesterol are not changed due to physical exercise-induced oxidative stress. The subjects, male endurance runners (n=24), performed a maximal treadmill test, and blood samples were taken before, during and after the run. Oxidized LDL lipids were measured by the diene conjugation method in lipids extracted from isolated LDL. Oxidized LDL lipids, μmol/L; oxidized LDL lipids/LDL cholesterol, μmol/mmol.
Figure 4:
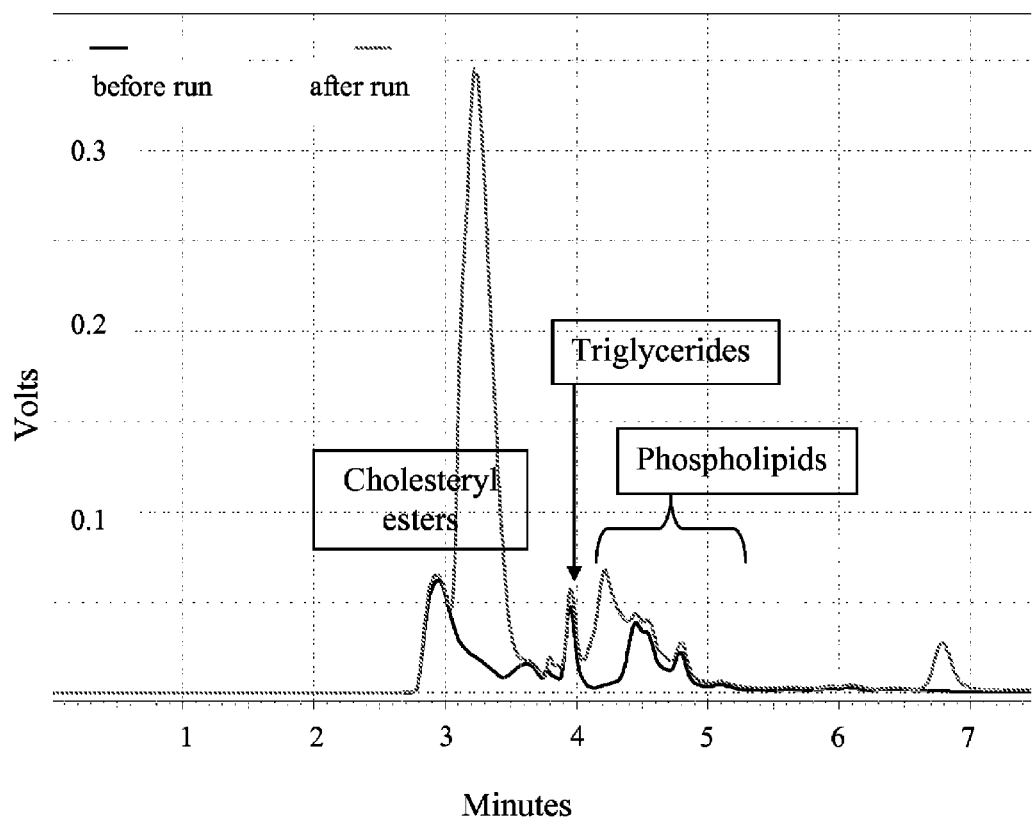
FIG. 4. HPLC analysis shows that the exercise-induced increase in oxidized HDL concentration is mainly due to increased levels of oxidized cholesteryl esters. The subject performed a maximal treadmill test, and blood samples were taken before and immediately after the run. Lipid classes were separated by HPLC (Shimadzu 10ADVP) on a Luna 5μ silica column. Detection was based on UV detector operating at 234 nm. The eluent was 4% propanol in hexane.

The aim of the first study was to investigate the lipid peroxide transporting function of LDL and HDL, the main carriers of endogenous lipids, under conditions of increased lipid peroxidation in human body in vivo. Physical exercise is known to increase lipid peroxidation, especially in actively functioning muscle tissues. The maximal treadmill test in the present study clearly elevated lipid peroxide levels of subjects, as verified by the increased concentration of the peroxidation indicator, malondialdehyde (before run MDA: 1.72±0.71; after run 2.41±1.12 µmol/L). Concentration of oxidized HDL lipids, and the ratio of oxidized HDL lipids/HDL cholesterol, increased substantially during the exercise, and were elevated still 90 min after the treadmill test (FIG. 2). Opposite to this, the concentration of oxidized LDL lipids, and the ratio of oxidized LDL lipids/LDL cholesterol were not increased by exercise (FIG. 3). On the contrary, there was a decreasing trend in the concentration of oxidized LDL lipids 90 min after the exercise. HPLC analysis showed that the exercise-induced oxidized HDL lipids were almost exclusively cholesteryl esters, with a minor contribution from the oxidized phospholipid fraction (FIG. 4). The increase in oxidized HDL was not due to impairment of antioxidant functions, since serum total antioxidant capacity (TRAP) of subjects rather increased during the exercise, and no decreases were seen in the concentrations of antioxidant vitamins.

Figure 5:
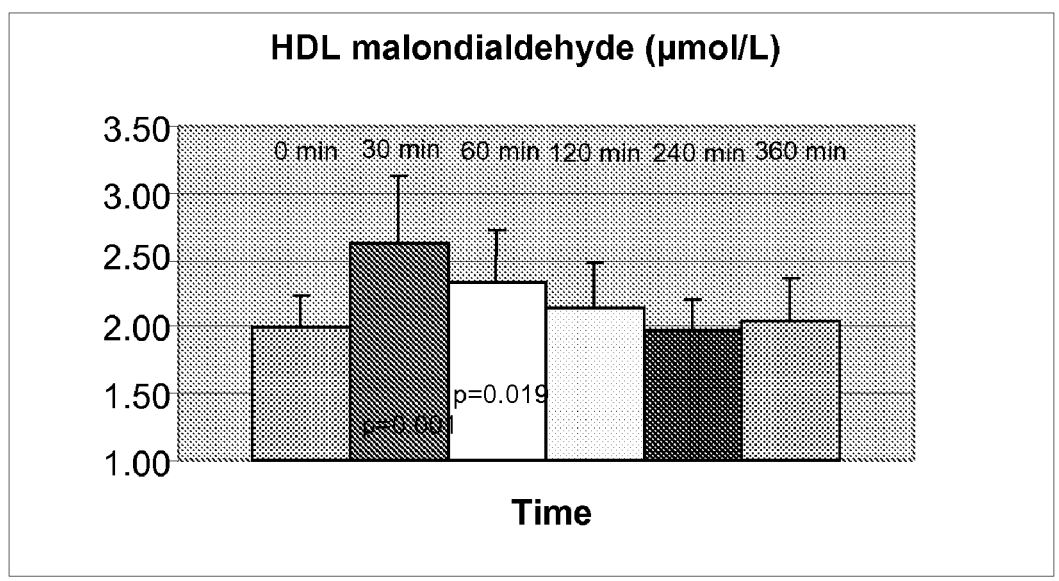
FIG. 5. Concentration of the water-soluble lipid peroxidation product malondialdehyde in HDL increases rapidly after ingestion of a meal rich in lipid peroxides. The test subjects (n=13) consumed a standard meal rich in lipid peroxides (a hamburger meal) and 4 dl of fruit juice. Blood samples were taken before the meal, and at 30, 60, 120, 240 and 360 min time points after the baseline measurement.
Figure 6:
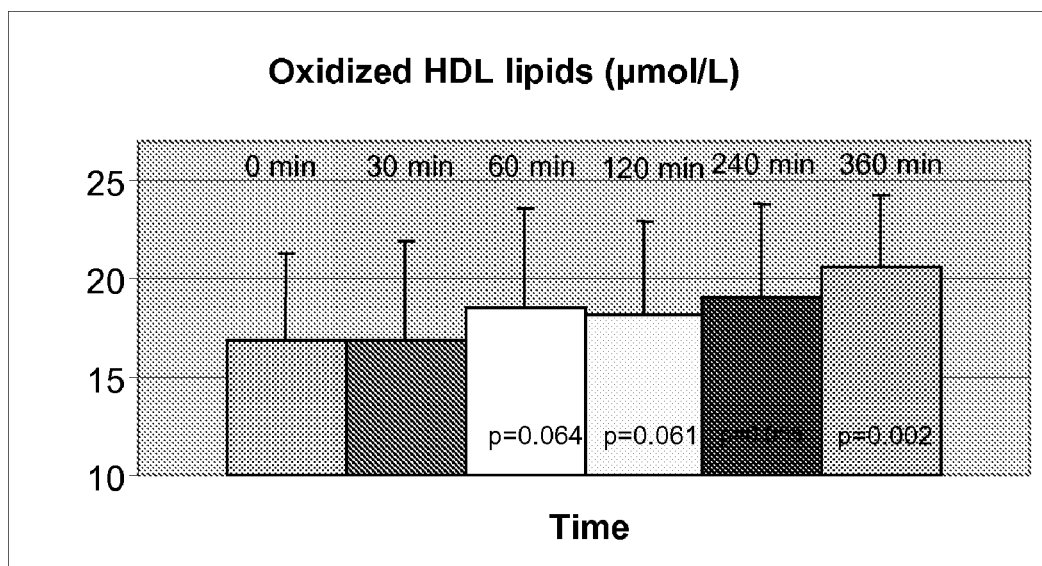
FIG. 6. The lipid soluble peroxidation products in HDL rise slowly, and are at highest level at the last time point. The test subjects (n=13) consumed a standard meal rich in lipid peroxides (a hamburger meal) and 4 dl of fruit juice. Blood samples were taken before the meal, and at 30, 60, 120, 240 and 360 min time points after the baseline measurement.

In the second study, another physiological experimental model was used, where the levels of lipid peroxides were increased due to ingestion of peroxide-rich food. For this purpose, human volunteers (N=13) consumed a standard hamburger meal (containing a total of 1300 µmol of lipid peroxides); blood samples were taken before and 30, 60, 120, 240 and 360 min after the meal. In parallel with physiological absorption mechanisms, concentrations of the water-soluble lipid peroxidation product, malondialdehyde, increased rapidly due to the meal, the peak concentration being at 30 min after meal (32%, p=0.001; FIG. 5). The lipid soluble peroxidation products in HDL increased slowly, and were highest at the last time point, 6 hours after consumption of the meal (22%, p=0.002; FIG. 6). This was another demonstration of the fact that HDL responds to elevated lipid peroxide concentrations by increasing the peroxide transport.

As an extension to this finding, the physiological significance of the peroxide removing function of HDL was further investigated. For this purpose, individuals with high/low basal HDL levels were compared to each other in the "peroxide-rich meal" model. It has been earlier found in this model that the amount of peroxidized lipids rise both in triglyceride rich fraction and LDL, reaching peak values 2 to 4 hours after the meal, whereafter the values gradually return to premeal levels. The peroxide-rich meal-induced increase in oxidized LDL lipids is potentially atherogenic, correlating strongly with BMI and insulin resistance. Subjects of the present study were divided into high and low HDL-cholesterol groups, and they were compared to each other with regard to the meal-induced effects on oxidized LDL lipids (expressed as the incremental area under the curve [iAUC 6 h] concentration of oxidized LDL lipids). It was found that among subjects with low basal HDL, the meal-induced rise in oxidized LDL lipids was significantly higher compared to those with high basal HDL (Table 1). It should be noted that the basal HDL level did not affect the postprandial elevation (iAUC 6 h) of triglyceride concentrations (Table 1). This finding is indicative of the fact that the lipid-peroxide removing function of HDL is significant for the clearance of lipid peroxidation products from the body.

TABLE 1

HDL attenuates peroxide-rich meal-induced elevation of oxidized LDL lipids

|  | Low HDL | High HDL |
|---|---|---|
| HDL cholesterol: Range | 0.72-0.99 mmol/L | 1.00-1.80 mmoml/L |
| HDL cholesterol: Mean ± SD | 0.81 ± 0.06 mmol/L | 1.12 ± 0.23 mmol/L[1] |
| Oxidized LDL lipids (iAUC 6 h) | 66.3 ± 38.8 | 33.2 ± 20.2[2] |
| Serum triglycerides (iAUC 6 h) | 3.12 ± 1.56 | 2.84 ± 1.51[3] |

[1]p < 0.001
[2]p = 0.008
[3]p = 0.695

Together, the above results show that the human body responds to increased presence of peroxidized lipids by transporting via HDL the excess of peroxidation products from tissues. This is a novel finding and demonstration of the fact that HDL acts as a physiological vehicle in the elimination of peroxidized lipids. This means that by measuring the concentration of oxidized HDL lipids it is possible to have a direct and accurate measure of the level of lipid peroxide-dependent oxidative state in tissues. This also means that the capacity of HDL to transport lipid peroxidation products is important for the body clearance of lipid peroxides and, hence, for the risk of lipid peroxide-related diseases.

Previous in vitro studies have shown that the intracellular peroxidized lipids are related to the inflammatory state at a cellular level. The aim of the third study was to investigate whether the concentration of oxidized HDL lipids would correlate with the inflammatory state in the body. For this purpose, the inflammation marker CRP was analyzed in serum samples from 62 healthy volunteers, and compared to oxidized lipoprotein lipid and serum lipid concentrations. It was found that CRP correlated with oxidized HDL lipids, but not with the oxidized LDL lipids, nor with the conventional serum lipids: total, LDL- and HDL-cholesterol or triglycerides (Table 2).

TABLE 2

Correlation of the inflammation marker hsCRP with oxidized lipoprotein lipids and serum lipids.

| Variable | Correlation (r) |
| --- | --- |
| Oxidized HDL lipids | 0.206 |
| Oxidized LDL lipids | 0.002 |
| Total cholesterol | 0.056 |
| LDL-cholesterol | 0.031 |
| HDL-cholesterol | 0.103 |
| Triglycerides | 0.015 |

The analyses were made in serum samples collected from 62 healthy 24-39 year old volunteers. This data show that the concentration of oxidized HDL lipids is related to the level of hsCRP, but hsCRP does not correlate with oxidized LDL lipids, nor with the conventional lipids.

A further analysis of the same study population was done by dividing the subjects into low, medium and high tertiles according to their oxidized lipoprotein lipid concentrations. The data showed that the levels of oxidized HDL lipids and CRP were closely related, while no such relation was found for CRP and oxidized LDL lipids (Table 3).

TABLE 3

Concentration of the inflammation marker hsCRP among individuals with low, medium or high levels of oxidized lipoprotein lipids.

| | Oxidized HDL lipids (µmol/L) | hsCRP (mg/L) |
| --- | --- | --- |
| Low HDL lipids: Range | 11.5-18.1 | |
| Low HDL lipids: Mean ± SD | 15.3 ± 1.9 | 1.02 ± 0.91 |
| Medium HDL lipids: Range | 18.3-22.2 | |
| Medium HDL lipids: Mean ± SD | 20.0 ± 1.1 | 1.37 ± 1.14 |
| High HDL lipids: Range | 22.2-42.2 | |
| High HDL lipids: Mean ± SD | 27.2 ± 5.0 | 2.77 ± 5.70 |
| Low LDL lipids: Range | 14.2-22.7 | |
| Low LDL lipids: Mean ± SD | 19.3 ± 2.6 | 1.19 ± 1.08 |
| Medium LDL lipids: Range | 23.4-31.9 | |
| Medium LDL lipids: Mean ± SD | 27.1 ± 2.9 | 2.51 ± 5.64 |
| High LDL lipids: Range | 32.1-75.9 | |
| High LDL lipids: Mean ± SD | 48.0 ± 26.4 | 1.40 ± 0.90 |

The analyses were made in serum samples collected from 62 healthy 24-39 year old volunteers. The study population was divided into six groups according to the oxidized lipoprotein lipid concentrations. The mean (± SD) oxidized HDL and LDL concentrations of the low, medium and high tertiles, as well as the mean hsCRP concentrations of the same individuals, are shown in the Table. The data show that the levels of oxidized HDL lipids and hsCRP are closely related. No such relation is found for CRP and oxidized LDL lipids.

Figure 7:
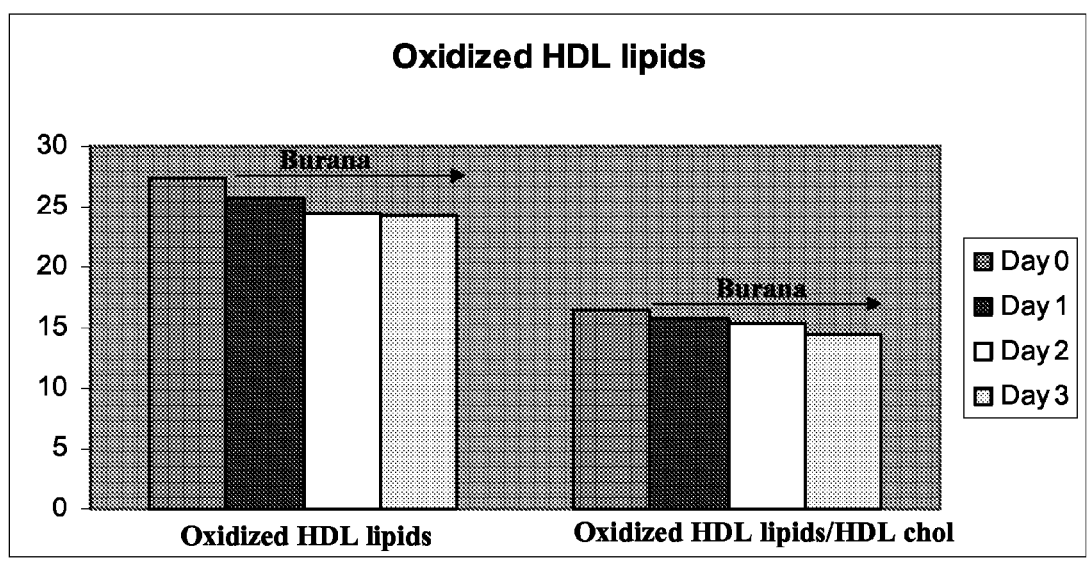
FIG. 7. The effect of anti-inflammatory drug treatment on concentration of oxidized HDL lipids and the ratio of oxidized HDL lipids/HDL cholesterol. Normolipidemic healthy volunteers (n=2) were given BURANA® (Orion, Finland) 3×400 mg/day for three consecutive days. Oxidized HDL lipids were measured by the diene conjugation method in lipids extracted from isolated HDL. Oxidized HDL lipids, μmol/L; oxidized HDL lipids/HDL cholesterol, μmol/mmol.

In the fourth study, human volunteers were treated with the anti-inflammatory drug BURANA®. In support of the working hypothesis, anti-inflammatory treatment decreased both the total amount of oxidized HDL lipids and the ratio of oxidized HDL lipids/HDL cholesterol (FIG. 7). Serum malondialdehyde concentration as well as the total antioxidant capacity remained unchanged. This result further confirms the fact that oxidized HDL lipids are related to the inflammatory state, and can be used for its estimation.

REFERENCES

1. Stocker, R. & Keaney, J. F. Jr. (2004) Role of oxidative modifications in atherosclerosis. *Physiol Rev* 84, 1381-1478.
2. Christison, J., Kajalainen, A., Brauman, J., Bygrave, J. & Stocker, R. (1996) Rapid reduction and removal of HDL- but not LDL-associated cholesteryl ester hydroperoxides by rat liver perfused in situ. *Biochem. J.* 314, 739-742.
3. Robbesyn, F., Garcia, V., Auge, N., Vieira, O., Frisach, M. F., Salvayre, R. & Negre-Salvayre, A. (2003) HDL counterbalance the proinflammatory effect of oxidized LDL by inhibiting intracellular reactive oxygen species rise, proteasome activation and subsequent NF-kappa B activation in smooth muscle cells. *FASEB J.* 17, 743-745.
4. WO 2005/055810 "Risk markers for cardiovascular diseases"
5. Nakano, T. & Nagata, A. (2003) Immunochemical detection of circulating oxidized high-density lipoprotein with antioxidized apolipoprotein A-I monoclonal antibody. *J. Lab. Clin. Med.* 141, 378-384.
6. Bergt, C., Nakano, T., Ditterich, J., DeCarli, C. & Eiserich, J. P. (2006) Oxidized plasma high-density lipoprotein is decreased in Alzheimer's disease. *Free Radical Biology & Medicine* 41, 1542-1547.
7. Ahotupa, M., Marniemi, J., Lehtimäki, T., Talvinen, K., Raitakari, O. T., Vasankari, T., Viikari, J., Luoma, J., Ylä-Herttuala, S. (1998) Baseline diene conjugation in LDL lipids as a direct measure of in vivo LDL oxidation. *Clin. Biochem.* 31, 245-261.

The invention claimed is:

1. A method for estimating in vivo lipid peroxide sequestering and transporting capacity of high density lipoprotein (HDL) in a subject, comprising obtaining a biological sample from the subject and measuring the concentration of oxidized HDL lipids in the biological sample, and estimating the in vivo lipid peroxide sequestering and transporting capacity of the subject's HDL from the measurement, wherein the higher the level of oxidized HDL lipids measured in the biological sample, the higher the in vivo lipid peroxide sequestering and transporting capacity of the HDL.

2. The method according to claim 1, wherein the biological sample is a serum or plasma sample.

3. The method according to claim 1 for diagnosis or follow-up of treatment or study of a lipid peroxide-related condition in the subject, wherein the measured concentration of oxidized HDL lipids in the subject is indicative of the clearance of lipid peroxides associated with the lipid-peroxide related condition from the body of the subject.

4. The method according to claim 3, wherein the condition is selected from the group consisting of atherosclerosis, cancer, neurodegeneration, diabetes, cataract, obesity and ageing.

5. The method according to claim 1, wherein the concentration of oxidized HDL lipids is measured by diene conjugation method in lipids extracted from isolated HDL.

* * * * *